US00PP10874P

United States Patent [19]

Deroose

[11] Patent Number: Plant 10,874

[45] Date of Patent: May 4, 1999

[54] VRIESEA PLANT NAMED 'ANNIE'

[76] Inventor: Reginald Deroose, Droogte 139, B-9940 Evergem, Belgium

[21] Appl. No.: 08/876,393

[22] Filed: Jun. 16, 1997

[51] Int. Cl.[6] ..... A01H 5/00

[52] U.S. Cl. ..... Plt./370

[58] Field of Search ..... Plt./88.8

[56] References Cited

U.S. PATENT DOCUMENTS

P.P. 10,368 4/1998 Deroose ..... Plt./88.8

OTHER PUBLICATIONS

GTITM UPOVROM Citation For 'Annie' as per NL PBR BRM0062; Jan. 16, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of Vriesea plant named 'Annie', characterized by its bright yellow inflorescence, with each bract being infused with red at its base, seven to ten branches each of which is about 10–12 cm in length, 35 to 45 cm total bract height, and its abundant medium green foliage in a dense rosette.

1 Drawing Sheet

The present invention comprises a new and distinct cultivar of Vriesea plant, referred to by the cultivar name 'Annie'. The genus Vriesea is of the family Bromeliaceae. 'Annie' is a product of a planned breeding program conducted in Evergem, Belgium by the inventor Reginald Deroose, and was originated from a cross between male parent Vriesea 'Marjan' (unpatented) and female parent Vriesea 'Katrien' (unpatented).

'Annie' was discovered and selected within the progeny of the stated cross by Reginald Deroose in 1989 is a controlled environment in Evergem, Belgium. Subsequent asexual reproduction of 'Annie' by tissue culture performed by Reginald Deroose in Evergem has demonstrated that the combination of characteristics as herein disclosed for 'Annie' are firmly fixed and retained through successive generations of asexual reproduction.

'Annie' has not been observed under all possible environmental conditions. The phenotype may vary significantly when grown under different conditions of temperature, light, and other determining factors, without, however, any variation in the genotype. The following observations, measurements and comparisons describe plants grown in Evergem, Belgium, under greenhouse conditions which closely approximate those generally used in horticultural practice.

The following traits have been repeatedly observed and are determined to be basic characteristics of 'Annie' which in combination distinguish this Vriesea as a new and distinct cultivar.

1. The inflorescence is bright yellow with some red at the base of each bract, and is about 35 cm to 45 cm in total height.

2. Each inflorescence has about 7 to 10 branches, each about 10–12 cm long.

3. The branches are numerous, with each branch being approximately 45° to the axis of the main stem.

4. Abundant medium green foliage in a dense rosette.

The new cultivar can be compared to the cultivar 'Charlotte', disclosed in applicant's pending application Ser. No. 08/668,626 (now U.S. Plant Pat. No. 10,368). Both cultivars have similar plant shape, yellow inflorescence infused with red, and green leaves. However, 'Annie' has more narrow leaves which bend downwardly more at the tips, the plant of 'Annie' is a little larger, the bracts of 'Annie' are at an approximately 45° angle to the main stem, and the inflorescence of 'Annie' is significantly larger and different in shape.

The accompanying color photographic drawing comprises a top perspective view of a typical plant of 'Annie' in bloom.

In the following description, color references are made to The Royal Horticultural Society Colour Chart, except where color terms of ordinary significance are used. The color values were determined between 1 p.m. and 2 p.m. in September 1990 under bright daylight conditions.

Classification:

*Botanical.*—Vriesea cv. 'Annie'.

*Commercial.*—Vriesea 'Annie'.

Parentage:

*Male parent.*—'Marjan'.

*Female parent.*—'Katrien'.

Propagation: Asexual propagation is preferably by tissue culture.

Plant:

*Form.*—Rosette

*Height.*—Approximately 40 cm to 45 cm in total height when grown in a 11 cm pot, and about 40 cm in diameter.

*Growth habit.*—Excellent, very vigorous.

*Foliage.*—Quantity: Abundant Size of leaf: 20 to 26 cm in length, about 3 cm wide. Shape of leaf: Oblong with tips bending down, rounded and apiculate. Surface texture: Glabrous Margin: Entire. Color: Upper side 147A; underside 137A Veins: Upper surface: slightly visible. Under surface: visible. Sheaths: Broad, distinct, green, much wider than blades.

Inflorescence:

*Total height.*—About 35 to 45 cm long.

*Bracts.*—Scape: Oriented erect to a little oblique, about 10 cm long and 1 cm in diameter, glabrous; 7 to 10 branches, each about 10–12 cm in length and 3.5 cm in width, color 13A, with the base being approximately 45A-B. Bract shape: Oval. Bract Size: 10–12 cm long and 3.5 cm wide, alternately arranged. Total bract height: 35 to 45 cm. Number of bracts: 7 to 10. Color: Mainly 13A, 45A-B at the base.

*Flowers.*—In the floral bracts, one flower per bract, typical for the genus Vriesea. Flowering is normally in progression from base to tip of scape or bracts, with many flowers at the same time. Flowers are transparent light yellow 12D-11D in color at the base to yellow 12A at the tip.

Reproductive organs:

*Stamens.*—1 per flower, color 2A.

*Pistels.*—6 per flower, color 17A. fragrance: None.

Resistance to disease: No disease problems have been noted to date.

I claim:

1. A new and distinct cultivar of Vriesea plant named 'Annie', as illustrated and described.

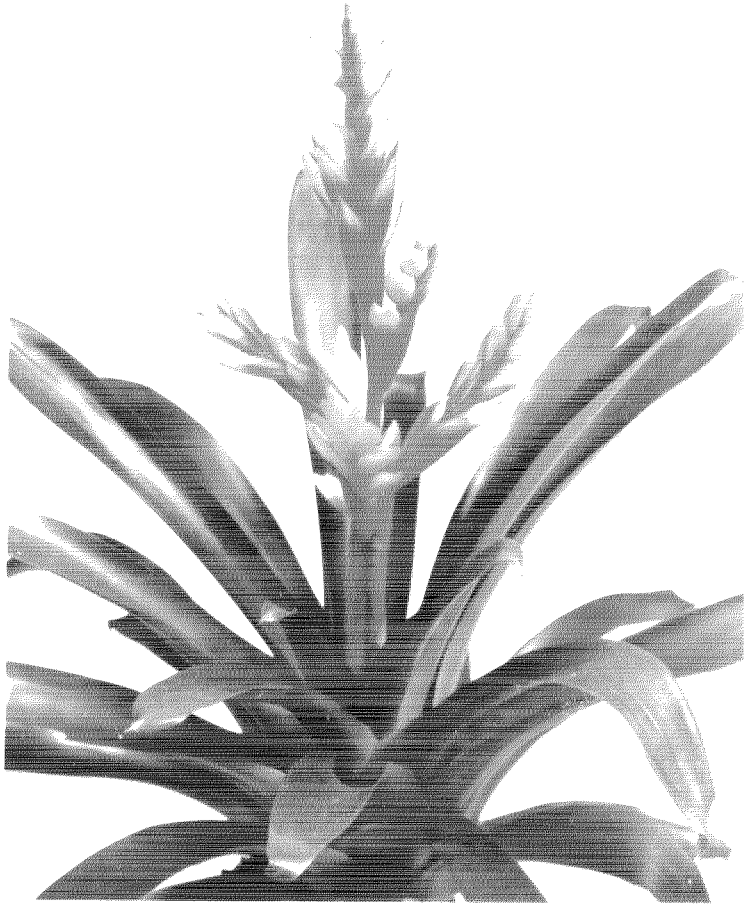

* * * * *